US006821513B1

(12) United States Patent
Fleming (10) Patent No.: US 6,821,513 B1
(45) Date of Patent: Nov. 23, 2004

(54) METHOD FOR ENHANCING HEMATOPOIESIS

(75) Inventor: William H. Fleming, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 213 days.

(21) Appl. No.: 10/019,165

(22) PCT Filed: Jun. 22, 2000

(86) PCT No.: PCT/US00/17427

§ 371 (c)(1),
(2), (4) Date: Dec. 20, 2001

(87) PCT Pub. No.: WO00/78930

PCT Pub. Date: Dec. 28, 2000

Related U.S. Application Data (60) Provisional application No. 60/140,628, filed on Jun. 23, 1999.

(51) Int. Cl.⁷ ................................................. C12N 5/00
(52) U.S. Cl. .................... 424/93.71; 435/1.1; 424/93.7; 424/93.73; 600/36; 623/1.1
(58) Field of Search ............................ 424/93.7, 93.71, 424/93.73; 600/36; 623/1.1; 435/1.1

(56) References Cited

U.S. PATENT DOCUMENTS

| | | |
|---|---|---|
| 3,993,078 A | 11/1976 | Bergentz et al. |
| 5,637,323 A | 6/1997 | Wiltrout et al. |
| 5,643,741 A | 7/1997 | Tsukamoto et al. |
| 5,750,397 A | 5/1998 | Tsukamoto et al. |
| 5,876,708 A * | 3/1999 | Sachs ........................ 424/93.1 |

FOREIGN PATENT DOCUMENTS

| | | |
|---|---|---|
| EP | 0 730 849 A | 9/1996 |
| WO | WO 97/22708 | 6/1997 |
| WO | WO 98/12304 A | 3/1998 |

OTHER PUBLICATIONS

Grimee and Wulfert., "Acute stress in rats produces a rapid and sustained increase in prostacyclin production in aortic tissue: dependence on corticosterone," *Life Sciences* vol. 57, No. 1, pp. 69–81, 1995.
Ohlstein et al., "SB209670, a rationally designed potent nonpeptide endothelin receptor antagonist," *Proceedings of the National Academy of Sciences of the United States* vol. 91, pp. 8052–8056, 1994.

* cited by examiner

Primary Examiner—Leon B. Lankford, Jr.
(74) Attorney, Agent, or Firm—Klarquist Sparkman, LLP (57) ABSTRACT

A method is provided for enhancing hematopoiesis. The method includes transplanting at least a therapeutically effective portion of an isolated vascular tissue into a subject, wherein the vascular tissue enhances hematopoiesis. A method is also provided for detecting an agent that affects hematopoiesis. The method includes transplanting a portion of an isolated vascular tissue into a subject, wherein the portion of the isolated vascular tissue is sufficient to enhance hematopoiesis. The vascular tissue is treated with an agent, and hematopoiesis is detected in the subject. Hematopoiesis in the subject is compared with hematopoietic in a control. A change in hematopoiesis in the subject as compared to the control indicatives that the agent affects hematopoiesis. A method is provided for isolating a hematopoiesis growth factor using the method of the invention. In addition, a method is provided for isolating a hematopoietic stem cell using the method of the invention. Pharmaceutical compositions and kits for promoting hematopoiesis are also disclosed. In addition, a non-human animal model is also disclosed for testing agents that affect hematopoiesis. The model system is a non-human animal deficient for hematopoiesis transplanted with an isolated portion of a vascular tissue, wherein the portion of the vascular tissue is sufficient to promote hematopoiesis.

16 Claims, 4 Drawing Sheets

Days Post Transplant

METHOD FOR ENHANCING HEMATOPOIESIS

PRIORITY CLAIM

This is a § 371 U.S. national stage of PCT/US00/17427 Jun. 22, 2000, which was published in English under PCT Article 21(2), which in turn claims the benefit of U.S. Provisional Application No. 60/140,628 filed Jun. 23, 1999.

FIELD OF THE INVENTION

This invention relates to the field of hematopoietic stem cells, specifically to the use of vascular tissue to reconstitute hematopoiesis in a subject.

BACKGROUND OF THE INVENTION

All the blood cells that circulate in the peripheral blood are derived from primitive mesenchymal cells referred to as hematopoietic stem cells. In the adult, most of these cells are located in the bone marrow. In the marrow of a healthy person, most stem cells are neither dividing nor differentiating. These cells are considered to be in a prolonged intermitotic interval and comprise the reserve stem cell pool that can be induced to divide upon hematopoietic stress.

Hematopoietic stem cells are self-regenerating, and also pluripotent in that they differentiate info several lineages, including lymphoid, myeloid and erythroid lineages. The lymphoid lineage, comprising B-cells and T-cells, provides for the production of antibodies, regulation of the cellular immune system, detection of foreign agents in the blood, detection of cells foreign to the host and the like. The myeloid lineage, which includes monocytes, granulocytes, megekaryocytes as well as other cells, monitors for the presence of foreign bodies in the blood stream, provides protection against neoplastic cells, scavenges foreign materials in the blood stream, produces platelets, and the like. The erythroid lineage provides the red blood cells, which act as oxygen carriers. Exposure to growth factors is believed to induce a stem cell to be dedicated to differentiate into a specific lineage.

The stem cell population is known to constitute only a small percentage of the total number of leukocytes in bone marrow. Recently, the mouse stem cell has been obtained in at least highly concentrated, if not a purified form, where fewer than about 30 cells obtained from bone marrow were able to reconstitute all of the lineages of the hematopoietic system of a lethally irradiated mouse. Indeed, one injected cell should be able to reconstitute all of the hematopoietic lineages.

SUMMARY OF THE INVENTION

There is a strong interest in identifying sources of hematopoietic stem cells, as possession of these sources will allow for identification of growth factors associated with its self-regeneration. In addition, there may be as yet undiscovered growth factors associated (1) with the early steps of dedication of the stem cell to a particular lineage; (2) the prevention of such dedication; and (3) the negative control of stem cell proliferation. The availability of new sources of stem cells can be extremely useful as a substitute for bone marrow transplantation, as well as in transplantation of other organs currently performed in association with transplantation of bone marrow. In addition, stem cells are important targets for gene therapy, where the inserted genes promote the health of the individual into whom the stem cells are transplanted. Identification of a new source of stem cells thus provides additional means of isolating cells useful in gene therapy. Isolation of a novel hematopoietic stem cell, or a novel intermediate in hematopoiesis, also provides new avenues for treatment of lymphomas and leukemias, as well as other neoplastic conditions, e.g., breast cancer. Model systems to isolate and test stem cells and hematopoiesis also provide a means for testing agents that affect stem cells.

A method is provided for enhancing hematopoiesis. The method includes transplanting at least a therapeutically effective portion of an isolated vascular tissue into a subject, wherein the vascular tissue enhances hematopoiesis.

In one embodiment, a method is provided for detecting agents that affect hematopoiesis. The method includes transplanting a portion of an isolated vascular tissue into a subject, wherein the portion of the isolated vascular tissue is sufficient to enhance hematopoiesis. The vascular tissue is treated with a candidate agent, and hematopoiesis is monitored in the subject. Hematopoiesis in the subject may be compared with hematopoiesis in a control subject, or compared to expected reference values, with reference to hematopoiesis in general or certain cell types (such as leukocytes, for example lymphocytes). A change in hematopoiesis in the subject as compared to the control indicatives that the agent affects hematopoiesis.

In another embodiment, a method is provided for isolating a hematopoietic growth factor. The method includes transplanting a portion of a vascular tissue into a subject, wherein the portion of the vascular tissue promotes hematopoiesis in the subject; and isolating a hematopoietic growth factor from the subject. Another embodiment is the hematopoietic growth factor itself, whether isolated by this approach or directly from the blood vessel itself.

In a further embodiment, a method is provided for isolating a hematopoietic stem cell. The method includes transplanting a portion of a vascular tissue into a subject, and isolating a hematopoietic stem cell from the subject.

A pharmaceutical composition is provided for promoting hematopoiesis that includes a therapeutically effective amount of an isolated vascular tissue in a pharmaceutically acceptable carrier. A method of making a pharmaceutical is also disclosed. The method includes obtaining a portion of a vascular tissue for use in enhancing hematopoiesis.

A kit is disclosed for promoting hematopoiesis. The kit includes a carrier means comprising a container which includes a portion of an isolated vascular tissue in a medium, such as a preservative medium that does not interfere with the hematopoietic activity of the vascular tissue. The use of an isolated blood vessel for hematopoiesis, is also disclosed, and this use can, for example, be disclosed in instructions included with the kit.

A non-human animal model is also disclosed for testing agents that affect hematopoiesis. The model system is a non-human animal deficient for hematopoiesis transplanted with an isolated portion of a vascular tissue, wherein the portion of the vascular tissue is sufficient to promote hematopoiesis. A method for generating the non-human animal model is also disclosed.

DETAILED DESCRIPTION OF THE SPECIFIC EMBODIMENTS

The following definitions and methods are provided to better define the present invention, and to guide those of ordinary skill in the art in the practice of the present invention. As used herein and in the appended claims, the singular forms "a", "an", and "the" include plural referents unless the context clearly dictates otherwise. Thus, for example, reference to "a cell" includes a plurality of such cells and reference to "the growth factor" includes reference to one or more growth factors, and so forth.

Unless defined otherwise, all technical and scientific terms used herein have the same meaning as commonly understood to one of ordinary skill in the art to which this invention belongs.

Definitions

Agent that affects hematopoiesis: A compound, antibody, nucleic acid molecule or protein that affects hematopoiesis. In one embodiment, the agent affects the growth, proliferation, maturation, or differentiation of hematopoietic cells. An agent can be a naturally occurring molecule or a synthetic molecule. In one specific, non-limiting example, the agent is a pharmaceutical compound. In another specific non-limiting example, the agent is a protein, such as a growth factor. In yet another specific non-limiting example, the agent is a nucleic acid molecule, such as an antisense or ribozyme molecule.

Animal: Living multicellular vertebrate organisms, a category which includes, for example, mammals and birds.

B Cell: A B cell is a lymphocyte, a type of white blood cell (leukocyte), that develops into a plasma cell, which produces antibodies.

Blood Vessel: The vessels through which blood circulates. In general, blood vessels are elastic tubular channels that are lined with endothelium. Blood vessels include the arteries, veins, and capillaries. Specific, non-limiting examples of a blood vessel include a vena cava, a thoracic aorta, a saphanous vein, a mammary artery, the brachial artery, and a capillary. In another embodiment, a blood vessel includes the smaller arteries and veins. In yet another embodiment, a blood vessel is a capillary of the microvascular circulation Differentiation: The process by which cells become more specialized to perform biological functions. Differentiation is a property that is often totally or partially lost by cells that have undergone malignant transformation.

Enhancement (enhancing): An increase in a particular parameter of a cell or organism. In one embodiment, enhancement refers to a 25%, 50%, 100% or greater than 100% increase in a parameter. In one specific, non-limiting example, enhancement of hematopoeisis refers to an increase in a population of the cells of a hematopoietic lineage (e.g. B cells, T cells, macrophages, monocytes, or a hematopoietic intermediate cell), such as a 25%, 50%, or 100% increase in the population of cells or the response of the population of cells.

Growth Factor. A "growth factor" is a substance that affects the growth of a cell or organism. In general, growth factors stimulate cell proliferation or maturation when they bind to their receptor ("growth factor receptor"). In one embodiment, growth factors are a complex family of polypeptide hormones or biological factors that are control growth, division and maturation of hematopoietic cells. In another embodiment, growth factors regulate the division and proliferation of cells and influence the growth rate of neoplastic tissue (e.g. cancer). A growth factor can be a naturally occurring factor or a factor synthesized using molecular biology techniques. In one specific, non-limiting example, a growth factor can be used stimulate lymphocyte production or differentiation, and thus can be used following chemotherapy or bone marrow transplantation.

Examples include growth factors, epidermal growth factor, platelet-derived growth factor, fibroblast growth factor. Insulin and somatomedin are also growth factors, the status of nerve growth factor is more uncertain. Perturbation of growth factor production or of the response to growth factor is important in neoplastic transformation.

A growth factor that affects the development (maturation), differentiation, division, or proliferation of hematopoietic cells is a "hematopoietic growth factor."

A "stem cell growth factor" is a growth factor that affects hematopoietic stem cells. Specific nonlimiting examples of a stem cell growth factor are c-kit ligand (e.g. steel factor, stem cell factor) also FLT-3 ligand and LIF.

Hematopoiesis: The formation and development of blood cells. Hematopoiesis involves the proliferation and differentiation from stem cells. In adult mammals hematopoeisis is known to occur in bone marrow. Hematopoiesis is the production of hematopoietic cells including B Cells, T cells, cells of the monocyte macrophage lineage, and red blood cells.

Immunologically Normal: "Immunologically normal" denotes an individual that displays immune system characteristics typical for the species to which the individual belongs. These characteristics would typically include, among others, functioning B-cells and T-cells as well as structural cell components, called cell surface antigens, which act as the immunologic signature for a particular organism.

The use of such immunologically normal recipients means that an immunologically normal recipient's immune system, via its B-(humoral response) and T-(cellular response) cells, will identify the cell surface antigens of a foreign cell or an engrafted tissue as foreign. This recognition leads ultimately to an immune response against the cell or tissue, resulting in destruction of the cell or rejection of the graft. An immune response against an allogeneic tissue is known as host-versus-graft rejection.

Immunologically Compromised: An "immunologically compromised recipient" is a subject with a genotypic or a phenotypic immunodeficiency. A genotypically-immunodeficient subject has a genetic defect which result in the inability to generate either humoral or cell-mediated response. A specific, non-limiting example of a genotypically immunodeficient subject is a genotypically immunodeficient mouse, such as a SCID mouse or a bg/nu/xid mice (Andriole et al., *J. Immunol.* 135:2911, 1985; McCune et al., *Science* 241:1632, 1988). In one embodiment, a genotypically immunodeficient subject is unable to react against a foreign cell or engrafted allogeneic tissue. A "phenotypically-immunodeficient subject" is a subject which is genetically capable of generating an immune response, yet has been phenotypically altered such that no response is seen. In one specific, non-limiting example, a phenotypically-immunodeficient recipient is irradiated. In another specific, non-limiting example, a phenotypically-immunodeficient subject has been treated with chemotherapy.

Inhibition (inhibiting): An decrease in a particular parameter of a cell or organism. In one embodiment, inhibition refers to a 25%, 50%, 100% or greater than 100% decrease in a parameter. In one specific, non-limiting example, inhibition of hematopoeisis refers to a decrease in a population of the cells of a hematopoietic lineage (e.g. B cells, T cells, macrophages, monocytes, or a hematopoietic intermediate cell), such as a 25%, 50%, or 100% decease in the population of cells or the response of the population of cells.

Isolated: An "isolated" biological component (such as a nucleic acid molecule, protein or portion of a vascular tissue) has been substantially separated or purified away from other biological components in the cell of the organism in which the component naturally occurs. Vascular tissue that has been isolated includes separation by surgical and/or enzymatic methods. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Lymphocytes: A type of white blood cell that is involved in the immune defenses of the body. There are two main types of lymphocytes: B-cell and T-cells.

Lymphoproliferation: An increase in the production of lymphocytes.

Mammal: This term includes both human and non-human mammals. Similarly, the term "subject" includes both human and veterinary subjects.

Monocyte: A large white blood cell in the blood that ingests microbes or other cells and foreign particles. When a monocyte passes out of the bloodstream and enters tissues, it develops into a macrophage.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Progenitor Cell: A "progenitor cell" is a cell that gives rise to progeny in a defined cell lineage. A "hematopoietic progenitor cell" is a cell that gives rise to cells of the hematopoietic lineage. One specific non-limiting example of a hematopoietic progenitor cell is a "common lynphoid progenitor cell," which is a progenitor cell that gives rise to immature and mature lymphoid cells. Another specific, non-limiting example of a hematopoietic progenitor cells is a "T cell progenitor cell," which gives rise to immature and mature T cells. Yet another specific, non-limiting example of a progenitor cell is a "strong progenitor cell," which is a progenitor cell that gives rise to stromal elements.

Stem Cell: A "stem cell" is a pluripotent cell that gives rise to progeny in all defined hematolymphoid lineages. In addition, limiting numbers of cells are capable of fully reconstituting a seriously immunocompromised subject in all blood cell types and their progenitors, including the pluripotent hematopoietic stem cell by cell renewal.

Subject: Any subject that has a vascular system and has hematopoietic cells in the wild-type organism. In one embodiment, the subject is a non-human mammalian subject, such as a monkey, mouse, rat, rabbit, pig, goat, sheep or cow. In another embodiment, the subject is a human subject.

Supernatant: The culture medium in which a cell is grown. The culture medium includes material from the cell, including secreted growth factors.

T Cell: A white blood cell critical to the immune response. T cells include, but are not limited to, $CD4^+$ T cells and $CD8^+$ T cells. A $CD4^+$ T lymphocyte is an immune cell that carries a marker on its surface known as "cluster of differentiation 4" (CD4). These cells, also known as helper T cells, help orchestrate the immune response, including antibody responses as well as killer T cell responses. $CD8^+$ T cells carry the "cluster of differentiation 8" (CD8) marker. In one embodiment, a CD8 T cells is a cytotoxic T lymphocytes. In another embodiment, a CD8 cell is a suppressor T cell.

Therapeutically effective portion or sufficient portion of a vascular tissue: An amount of a vascular tissue, that can be determined by various methods, including generating an empirical dose-response curve, predicting potency and efficacy of using modeling, and other methods used in the biological sciences. In general, a therapeutically effective portion of a blood vessel is an amount sufficient to reconstitute hematopoeisis in an immunocompromised subject. In one embodiment, a therapeutically effective amount of vascular tissue is a blood vessel that includes at least one of the intima, media, or adventitia.

In one specific, non-limiting example, the graft is a vessel that is 1 mm to about 10 cm in length, or is less than 1 cm in length, or is about 2 mm to about 4 mm in length. In another specific, non-limiting example, the vessel has a circumference of less than about 0.5 mm, or a circumference of about 0.5 mm to about 2.5 mm. In one embodiment, the graft has a circumference of about 1.0 mm to about 2.0 mm.

In yet another specific, non-limiting, example the area of the vascular tissue utilized is about 1 mm$^2$ to about 1 cm$^2$, or is about 1 mm$^2$ to about 100 mm$^2$, or is about 1 to about 10 mm$^2$, or is about 6 to about 8 mm$^2$, or is about 7 mm$^2$. In a further specific, non-limiting, example the vascular tissue weighs about 1 to about 50 mg, or weighs about 5 to about 20 mg, or weights about 10 mg. In another specific, non limiting, example the vascular tissue contains about $1 \times 10^5$ cells to about $1 \times 10^9$ cells, or contains about $1 \times 10^6$ to about $1 \times 10^8$ cells, or contains about $1 \times 10^7$ cells. In one embodiment, the therapeutically effective amount of a vascular tissue is a 4 mm long portion of vena cava or a thoracic aorta.

The therapeutically effective portion of a vascular tissue will be dependent on the type of vascular tissue utilized (e.g artery, vein or capillary), the subject being treated (e.g. the species or size of the subject), the degree that the subject is immunocompromised, and the location of the transplant (e.g. intraperitoneal, kidney capsule, etc).

Specific assays for determining the therapeutically effective portion of a vascular tissue are provided herein. In one specific, non-limiting example, different lengths, volumes or weights of vascular tissue are transplanted under the kidney capsule of an immunocompromised subject, and the presence and/or quantity of hematopoietic cells (which can include subtypes of hematopoietic cells) is detected and/or analyzed. The methods disclosed in the present invention have equal application in medical and veterinary settings. Therefore, the general term "subject being treated" is understood to include all animals (e.g. humans, apes, dogs, cats, mice, rats, rabbits, sheep, pigs, and cows) and reconstitution of hematopoiesis is monitored using the assays described herein. For example, the presence of B cells, T cells, or macrophages following transplantation can be determined.

Transplantation: The transfer of a tissue or an organ, or a portion thereof, from one body or part of the body to another body or part of the body. An "allogeneic transplantation" or a "heterologous transplantation" is transplantation from one individual to another, wherein the individuals have genes at one or more loci that are not identical in sequence in the two individuals. An allogeneic transplantation can occur between two individuals of the same species, who differ genetically, or between individuals of two different species. An "autologous transplantation" is a transplantation of a tissue or a portion thereof from one location to another in the same individual, or transplantation of a tissue or a portion thereof from one individual to another, wherein the two individuals are genetically identical.

Vascular Tissue: Tissue consisting of, or containing, vessels as an essential part of a structure. Vascular tissue operates by means of, or is made up of an arrangement of, vessels. Vascular tissue includes the arteries, veins, capillaries, lacteals, etc. In one embodiment, vascular tissue includes a highly vascularized organ (e.g. the lung). In another embodiment, vascular tissue is a blood vessel, or a portion thereof. A "portion" of a blood vessel is any length less than the full length of the vessel in its native location, and includes portions of the blood vessel that do not form an enclosed lumen. Cells isolated from a vascular tissue are a population of cells isolated from the remaining components of the tissue. One specific, non-limiting example of cells from a vascular tissue are endothelial cells isolated from vascular tissue, such as a blood vessel.

Method for Enhancing Hematopoiesis

A method is provided herein for enhancing hematopoiesis, comprising transplanting at least a therapeutically effective portion of an isolated vascular tissue into a subject, wherein the vascular tissue enhances hematopoiesis. The minimum therapeutically effective amount of a vascular tissue can be determined using the model system described herein. The minimum therapeutically effective amount of a vascular tissue can be utilized to enhance hematopoiesis, or a larger portion of a vascular tissue can be utilized.

In one embodiment, the subject can be an immunologically normal subject. In another embodiment the subject is immunocompromised (e.g. a phenotypically or genetically immunocompromised subject). The subject may be generally immunocompromised, so that the responses of all of the cells of the immune system are impaired, or the subject may be immunocompromised in one particular aspect of the immune response, such as the responsiveness of a specific cell type. In one specific, non-limiting example, T cell responses are impaired. In another specific, non-limiting example, B cell response is impaired. In yet another specific, non-limiting example, a monocyte or macrophage response is impaired. It should be noted that there are many assays to test responsiveness of specific cells of the immune system, and that one of skill in the art can readily determine a test to assess responsiveness of a population of cells of the immune system in a subject. Specific non-limiting examples of tests to assess the immune system are a test for cytotoxic T lymphocyte activity (CTL assays) such as a chromium release assay, an assay for mixed lymphocyte response (MLR assay), an assay for helper cells, an assay for cytokine secretion, an assay for immunoglobulin production, or an assay to detect antigen presenting cells (APCs). One specific non-limiting example of an immunocompromised subject is a subject deficient in hematopoiesis as a result of irradiation or the use of chemotherapeutic agents.

A vascular tissue is transplanted into the subject, or from one location in the subject to another ectopic (away from its normal) location in the subject. In one embodiment, the vascular tissue is an isolated vessel, or an hematopoietic effective portion thereof. Specific non-limiting examples of vessels are the vena cava, the thoracic aorta, the mammary artery, the saphenous vein, or a capillary. In another embodiment, the vascular tissue is a portion of a highly vascularized organ. One of skill in the art can readily determine a therapeutically effective portion of vascular tissue using the model system derived herein.

The site of transplantation is selected so that hematopoiesis is enhanced by the grafted vascular tissue. In one embodiment, the vascular tissue is transplanted under the kidney capsule. In another embodiment, the vascular tissue is transplanted into the peritoneum. In a further embodiment, the vascular tissue is transplanted subcutaneously.

Enhancement of hematopoiesis can be measured by any assay known to one of skill in the art. Specific, non-limiting examples of assays are the examination of the spleen for macroscopic colonies (CFU-S). Alternatively, fluorescence activated cell sorting can be performed to assess the presence of a population of lymphocytes. Assays for B and T cell activity can also be utilized. As described above, specific non-limiting examples of assays for hematopoietic cells are an assay for cytotoxic T lymphocyte (CTL assay, such as a chromium release assay), an assay for mixed lymphocyte response (MLR assay), an assay for helper cells, an assay for cytokine secretion, an assay for immunoglobulin production, or an assay to detect antigen presenting cells (APCs).

Animal Models

In one embodiment, the methods described herein are used to produce a non-human animal model for testing agents that affect hematopoiesis. To make the model, a non-human animal deficient for hematopoiesis is transplanted with an isolated portion of a vascular tissue, wherein the portion of the vascular tissue is sufficient to promote hematopoiesis.

In one embodiment, non-human animal is a mammal. Specific non-limiting examples of a animal is a mouse, rat, rabbit, cat, dog, pig, goat, sheep, or a monkey. The non-human animal is deficient in hematopoiesis, and can be genetically or phenotypically immunocompromised. Several species of animals are known to have a genotypic immunodeficiency. One specific, non-limiting animal with a genotypic immunodeficiency is a SCID mouse. Similarly, methods are known in the art to create a phenotypic immunodeficiency. Specific, non-limiting examples of treatments to create a phenotypic immunodeficiency are the irradiation of a non-human mammal or the treatment with a chemotherapeutic agent of a non-human animal.

The methods and model systems described herein can be used to assess the effect of an agent on hematopoiesis. In order to assess the effect of an agent on hematopoiesis, a therapeutically effective portion of an isolated vascular tissue is transplanted into a subject, such as a genetically or phenotypically immunocompromised subject. In one embodiment, the portion of the isolated vascular tissue is known to be an amount sufficient to enhance hematopoiesis. The vascular tissue is treated with the agent. Treatment can occur prior to, or subsequent to, engraftment of the vascular tissue. If the vascular tissue is treated after transplantation, treatment with the agent can be local or systemic. Systemic treatment can occur by any route known to one of skill in the art, including intravenous, subcutaneous, intramuscular, or intraperitoneal injection.

Following treatment with the agent, hematopoiesis is detected in the animal. Hematopoiesis can be detected by any means known to one of skill in the art. One specific non-limiting example of an assay of use is fluorescence activated cell sorting. FACS analysis can be performed to detect for any population of hematopoietic cells (e.g., T cells, B cells, granulocytes, macrophages, an immature population of T or B cells). Another specific, non-limiting example of an assay of use is a CFU-S assay (see the Examples below). Yet another specific, non-limiting assay of use is an assay the measures red blood cells or a parameter thereof, such as a test to measure hemoglobin concentration, red blood cell count and red blood cell half-life (such as conventional detection of a peripheral red blood cell count).

Hematopoiesis in the treated subject is then compared with a control value of hematopoiesis. In one embodiment, the control value is obtained from a normal subject, that is not transplanted nor treated with the agent. In another embodiment, the control value is obtained from an immunologically compromised subject transplanted with a therapeutically effective portion of an isolated vascular tissue, but not treated with the agent. In yet another embodiment, the control value is obtained from non-transplanted subject that is treated with the agent. In a further embodiment, the control value is a compilation of data points, the value of which is used for comparison purposes (e.g. a standard value). Any change in any parameter of hematopoiesis in the treated subject as compared to the control is indicative that the agent affects hematopoiesis.

Kits

The methods of the invention are ideally suited for the preparation of a kit. Such a kit may comprise a carrier means, such as a box, bag, or plastic carton, containing one or more container means such as vial tubes, and the like. Each of the container means can include a separate element to be used in a method. For example, one of the container means can include a portion of a vascular tissue. The kit may also contain a container means with a buffer or vehicle for the introduction of the vascular tissue. In addition, instructions can be provided to detail the use of the components of the kit, such as written instructions, video presentations, or instructions in a format that can be opened on a computer (e.g. a diskette or CD-ROM disk).

Without further elaboration, it is believed that one skilled in the art can using this description, utilize the present invention to its fullest extent. The following examples are illustrative only, and not limiting of the remainder of the disclosure in any way whatsoever.

SPECIFIC EXAMPLES

Example 1

Production of an Animal Model

The yolk sac is the first site of recognizable hematopoiesis in the developing mammalian embryo. In the mouse, mesodermal cells aggregate and, by day 7 of gestation, form the extraembryonic blood islands. Differentiation of these mesodermal elements gives rise to the endothelium and the first primitive globinized erythrocytes. As the yolk sac vascular network grows it directly communicates with the distal aorta of the developing embryo, thereby linking the extreambryonic and intraembryonic vascular systems. The yolk sac is the primary site of erythropoiesis during embryonic development, then hematopoietic precursors are thought to migrate and subsequently colonize the liver beginning as early as day 9. The liver then becomes the primary site of hematopoiesis during fetal development until late in gestation, when the medullary cavity of the bones is formed and seeded with hematopoietic precursors from the fetal liver. By the end of gestation, the bone marrow has become the principal site of hematopoiesis and continues to produce blood cells throughout the lifetime of higher vertebrates. This model is based on the orderly migration of hematopoietic precursors as determined primarily by morphologic studies of erythropoiesis during embryonic and fetal development. Modem transplantation studies however have revealed that hematopoietic stem cell development is more complex.

Although the bone marrow is thought to be the principal site of hematopoiesis in adult mammals, in a number of disease states significant blood cell production occurs outside the medullary cavity of the bone. This extramedullary hematopoiesis (EMH) is encountered most frequently in myelofibrosis, a neoplastic disorder characterized by the replacement of the marrow cavity with fibrous tissue. In addition, the abnormal hemoglobin synthesis found in severe β-thalassemia results in a marked increase of ineffective red blood cell production and the subsequent expansion of hematopoiesis to extramedullary sites (Cardia et al., Pediatr. Neurosurg. 20:186–189, 1994). It has been postulated that quiescent hematopoietic stem cells reside in the adult liver or, alternatively, that bone marrow derived HSC can migrate to the liver as a consequence of hematopoietic stress.

During embryogenesis, the close proximity of developing blood vessels and early sites of hematopoiesis have led to the hypothesis of a common precursor cell or hemangioblast that is present in the embryo. In order to determine if a population of hematopoietic progenitor/stem cells persists in association with the vascular system of the adult, an assay was performed to determine if functional hematopoietic cells were present in the blood vessels of normal adult mice.

It is known that when mice are phenotypically immunocompromised, such as by treatment with high doses of radiation, a marked depletion of hematopoietic progenitor cells and stem cells within the bone marrow is observed. This depletion of cells is accompanied by the production of a number of cytokines and growth factors that facilitate engraftment of transplanted donor hematopoietic cells (such as stem cells isolated from the bone marrow) into the irradiated hematopoietic microenvironment. It has previously been demonstrated that irradiated recipient mice will die within 3 weeks from bone marrow failure if they are not transplanted with a sufficient number of primitive donor hematopoietic cells. Conversely, almost three logs more donor cells must be transplanted into intact non-irradiated mice before donor cells will engraft in active sites in the bone marrow and contribute to steady state hematopoiesis (Ramshaw et al., Blood 86:924–929, 1995).

A model system was thus developed, using irradiated mice, to demonstrate for the first time that functional hematopoietic cells are present in the vascular tissue. In order to demonstrate that the hematopoietic microenvironment in irradiated mice could stimulate and recruit hematopoietic progenitor cells from vascular tissue, 4 mm segments of proximal inferior vena cava (VC) or thoracic aorta (TA) were harvested from normal adult donor mice. The isolated vascular tissue was transplanted intact under the kidney capsule of lethally irradiated adult recipient mice.

The transplanted mice were sacrificed at 14 days post-transplant, and histogical sections were prepared of the graft and the surrounding tissue. The examination of the vascular implant revealed significant disruption of the normal architecture of the vessel wall. A large accumulation of a diverse population of cells was observed within the wall of the graft. In addition to the presence of a diffuse infiltrate of morphologically indistinct cells, the clear development of thin walled vascular channels, similar to hemangiomas, was observed. In contrast, when VC or TA tissue was transplanted under the kidney capsule of non-irradiated mice, the normal architecture was essentially maintained, indicating that the accumulation of cells within the wall of the transplanted vascular tissue was specifically induced by radiation treatment of the recipient. The accumulation of cells and the development of vascular channels in the wall of the vascular graft were consistent with the proliferation and differentiation of a population of cells within the vascular graft. However, is also possible that a population of host cells in the irradiated recipient may have migrated to and proliferated within the transplanted vascular tissue.

Example 2
Cells Migrate from Transplanted Vascular Grafts

To determine if cells from the vascular grafts migrated and differentiated, a portion of the vena cava or thoracic aorta was surgically isolated from ROSA26 mice, which constituitively expressed a β-galactosidase transgene with a CMV promoter (Zambrowicz et al., Proc. Natl. Acad. Sci. 94:3789–3794, 1997). The isolated vascular tissue was transplanted into the kidney of C57BL/6 mice. The recipient kidney containing the vascular graft was removed 14 days after transplantation, fixed, sectioned, and incubated with the enzyme substrate X-gal, which is converted to a blue precipitate in the presence of β-galactosidase.

The majority of the cells in the ROSA-26 TA graft were blue and therefore donor derived. In addition, a significant population of donor cells was observed migrating under the kidney capsule away from the initial transplantation site, consistent with a response to signals from the irradiated host microenvironment. To demonstrate that large numbers of host cells had not infiltrated into the donor vascular tissue, a portion of the vena cava from normal adult donors was transplanted under the kidney capsule of irradiated ROSA26 recipients. These vascular grafts did not significantly react with X-gal confirming that this accumulation of cells was primarily of donor origin. Histologic evaluation of the ROSA26 grafts confirmed the presence of primarily donor-derived cells in these vascular grafts. Taken together, the results demonstrate an expansion of donor-derived cells in both donor vena cava and thoracic aorta following transplantation into irradiated recipients.

Example 3
Vasular Tissue Grafts Give Rise to Colony Forming Cells in the Spleen

Figure 1:
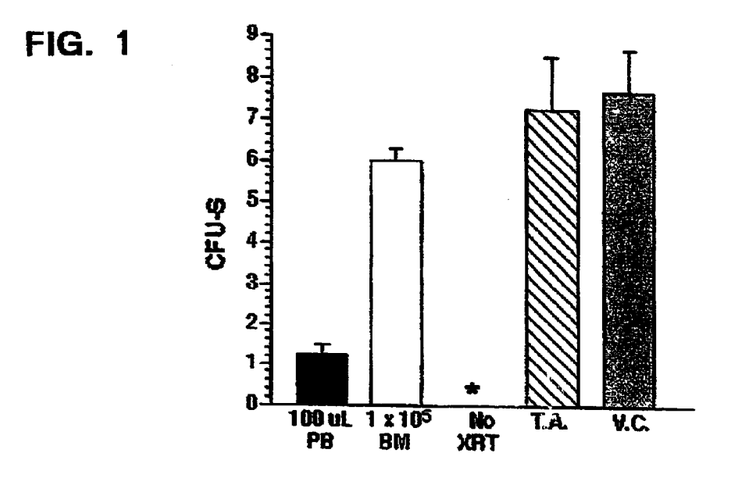
FIG. 1 is a bar graph showing the spleen colony forming activity of transplanted vascular tissue. Irradiated recipients were transplanted with either 100 µL untreated PB, $1 \times 10^5$ BM cells, a 4 mm thoracic aorta (TA) or vena cava (VC) graft, or a 4 mm segment of VC with no irradiation treatment. Spleens were harvested on day 14 post-transplant and the number of CFU-S per spleen were determined. Mean and SEM for each treatment group are shown. No colonies were seen in non-irradiated transplant recipients. PB=peripheral blood. BM=bone marrow. TA=thoracic aorta. VC=vena cava. No XRT=TA or VC grafts in nonirradiated recipients.

Diverse sources of hematopoietic stem cells including bone marrow (BM), fetal liver, and peripheral blood (PB), produce macroscopic spleen colonies (CFU-S) 12–14 days after injection into irradiated mice. Each colony is clonal and an average of 5 colonies per spleen arise from the injection of $1\times10^5$ BM cells (see Till and McCulloch, Radiat. Res. 14:213, 1961; Siminovitch et al., J. Cell. Comp. Physiol. 62:327, 1963). The potential of both vena cava (VC) and thoracic aorta (TA) grafts to give rise to CFU-S was determined and directly compared to $1\times10^5$ BM cells or 100 $\mu$l of unfractionated normal PB. Cohorts of irradiated recipient mice received either a 4 mm vascular graft (TA or VC) under the kidney capsule, $1\times10^5$ BM cells by i.v. injection, or 100 $\mu$L PB by i.v. injection. Spleen colonies were enumerated on day 14; the mean number of colonies derived was similar for transplanted VC, TA, and BM ranging from 6.1–7.8 colonies per spleen (FIG. 1). In this model system, radiation (e.g. an immunocompromised subject) was required for the development of day 14 CFU-S in recipients of VC or TA grafts.

To ensure that endogenous spleen colonies did not arise in animals treated with this radiation dose (1100cGy), the spleens from non-transplanted, irradiated control animals were examined and no colonies were detected. In contrast with the VC, TA and BM transplants, a mean of only 1.2 colonies per spleen were detected following the injection of 100 $\mu$l of PB.

Normal adult peripheral blood does contain small numbers of circulating hematopoietic stem cells (Goodman and Hodgson, Blood 19, 702–714. 1962). Although the vascular tissue grafts were extensively rinsed to remove residual donor blood, we directly demonstrated that contaminating donor PB was not a significant source of day 14 spleen colonies in these experiments. The maximum volume of blood in the lumen of a VC or TA graft (4 mm×0.7 mm) is 1.5 µl. The injection of almost 66-fold excess (100 µl) of the maximal amount of blood present in these vascular grafts gave rise to only 1.2 colonies per spleen. This experiment indicates that the frequency of cells that give rise to day 14 CFU-S is >300-fold higher in the transplanted vascular grafts than in normal peripheral blood.

Figure 2:
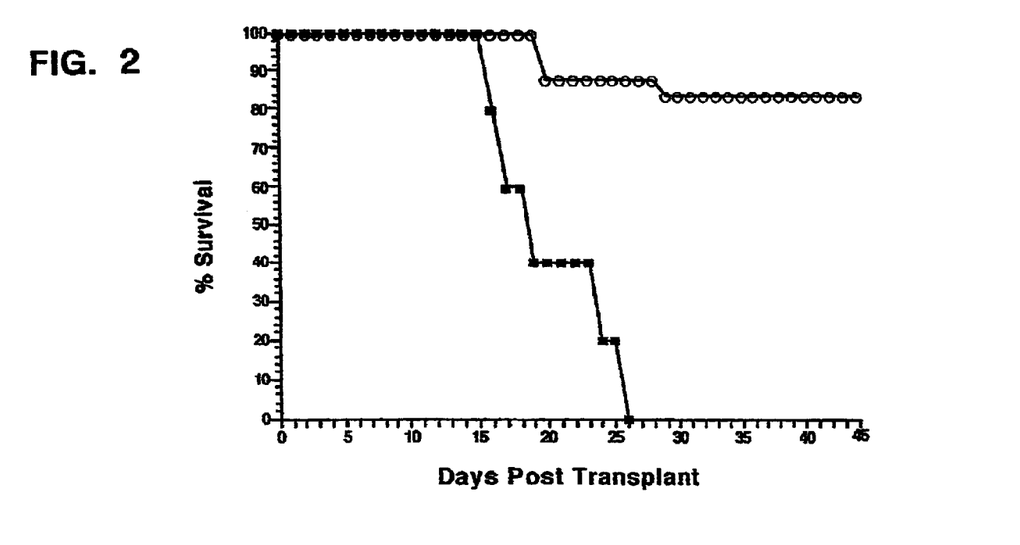
FIG. 2 is a graph of percent survival of transplanted mice tested using a Radioprotection assay. Irradiated recipients were transplanted with 4 mm segments of aorta or vena cava (○). Control animals received 100 µL untreated PB (■). The percent surviving over time is shown.

Example 4
Vascular Grafts Confer Protection Against Lethal Irradiation: A Portion of a Vascular Tissue is Sufficient The injection of a sufficient number of hematopoietic stem cells into lethally irradiated recipient mice protects them from death secondary to bone marrow failure. To evaluate the potential of transplanted vascular tissue to protect mice from radiation induced death, sections of 4 mm in length (an area of 1.88 mm$^2$) of either VC or TA were transplanted under the kidney capsule of lethally irradiated recipients (1100cGy in 2 fraction given 3 hours apart). Control mice were injected with 100 µl of unfractionated PB. Transplant recipients were maintained on antibiotic water under sterile conditions and their survival monitored daily for 45 days (FIG. 2). All mice transplanted with 100 µl of PB died between day 15 and day 26, consistent with the time course of radiation induced marrow failure. A similar result was seen in mice that were irradiated but not transplanted. In contrast, 85% of the recipients of vascular grafts survived. These results demonstrate a dramatic increase in survival with the transplantation of relatively small explants of normal large blood vessels (VC and TA) have the capacity to protect mice from radiation induced bone marrow failure.

Example 5
Vascular Grafts Attenuate Radiation Induced Bone Marrow Failure

Figure 3A:
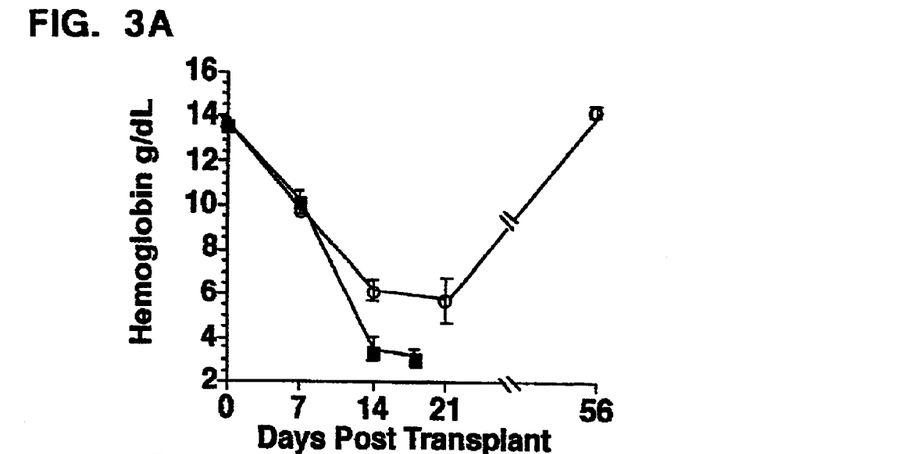
FIG. 3 is a graph showing the results of a peripheral blood analysis. Irradiated recipients were transplanted with 4 mm segments of thoracic aorta or vena cava. Control animals received radiation alone. The peripheral blood of recipient mice was examined on day 7, 14, 21, and 56. Each group of mice was examined at one time point only to eliminate the effects of serial phlebotomy. Panel A documents the detection of red blood cells (hemoglobin). Panel B documents the detection of white blood cells (WBC). Panel C documents detection of platelets. (Mean±SEM for each group are shown).
Figure 3B:
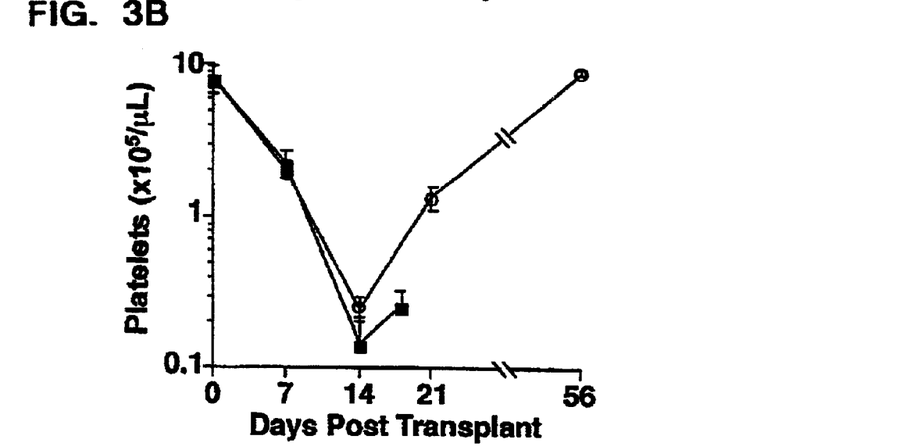
Figure 3C:
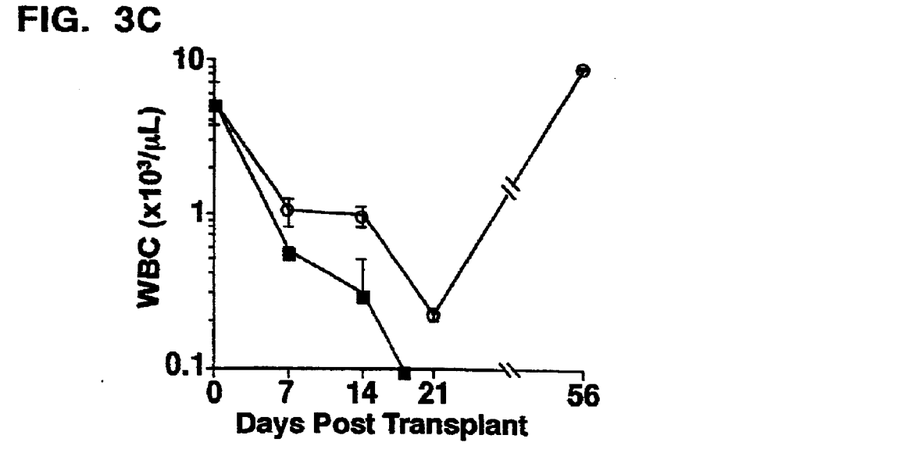

Lethally irradiated mice primarily die due to severe anemia and bleeding from low platelet counts. To evaluate the effects of the transplantation of vascular tissue on the leukocytes, red cells and platelets in the peripheral circulation, cohorts of mice were treated with radiation and then transplanted with VC or TA grafts. A group of control mice was irradiated but not transplanted. At the time points indicated, cohorts of mice were bled and analyzed. Each group of mice was analyzed at one time point only to avoid the effects of repeated phlebotomy on the hemoglobin (Hb) concentration. Irradiated control mice were evaluated only until day 18 as an insufficient number of mice survived longer than this time point. The results are shown in FIG. 3. When the Hb concentration was assayed at day 7, a similar decrease was observed in both transplant recipients and control mice. By day 14 however, the Hb was 6.2 g/dL in the vascular graft recipients but only 3.4 g/dL in the control group. Only a modest further decline was noted in irradiated non-transplanted recipients that survived until day 18 (a Hb of ~3.0 g/dL represents the severest anemia compatible with survival in this mouse strain). Vascular graft recipients maintained a Hb concentration of about 2-fold higher than the threshold of 3.0 g/dL, consistent with the production of donor derived red blood cells. When the number of circulating platelets was determined, a similar decrease in platelet count was observed in both the transplanted and non-transplanted groups up to day 14. By day 21 however, the number of platelets had increased 7-fold above the day 14 value in the vascular graft recipients. Evaluation of the number of white blood cells revealed that a higher number of circulating cells was observed in the vascular graft recipients at all time points examined. As shown in FIG. 2, irradiated non-transplanted mice typically died from complications of pancytopenia within 21 days after radiation treatment. In contrast, the majority of VC and TA recipients survived and demonstrated a normal Hb, platelet and white blood cell counts 2 months after transplantation.

Example 6
Multilineage Hematopoietic Reconstruction After Vascular Transplantation The role of donor derived cells in reconstituting the hematopoietic system of irradiated mice was further invested using donor and recipient mice that were congenic at the Ly5 locus (CD45). Ly5.2 donor VC or TA grafts were implanted under the kidney capsule of irradiated Ly5.1 recipients. Peripheral blood and spleen tissue was harvested at different time intervals and the frequency of donor derived cells was evaluated. Using flow cytometry, the frequency of Ly5.1 host cells and Ly5.2 donor cells expressing T-cell (CD3), B-cell (B220) and myeloid (Mac-1/Gr-1) markers was determined (see FIG. 4).

Figure 4A:
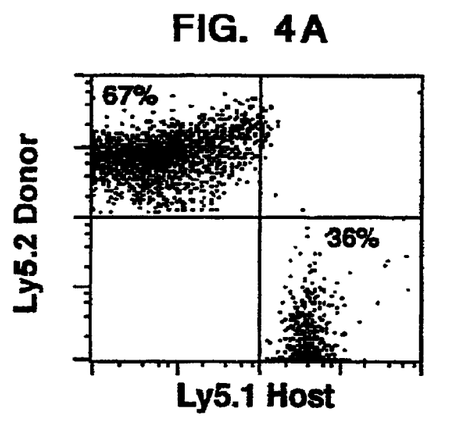
FIG. 4 shows plots of data obtained by fluorescence activated cell sorting (FACS). These plots demonstrate the detection of donor derived cells in transplant recipients. Panel A shows the percent donor cells (Ly5.2) detected in the PB of a vena cava recipient three weeks after transplantation. Panels B–D show multilineage reconstitution in the spleen of an aorta graft recipient four months after transplantation. The percentage of donor cells expressing B220 (Pannel B), CD3 (a T cell marker, Panel C), or Mac-1/Gr-1 (a macrophage/granulocyte marker, Panel D) are shown.
Figure 4B:
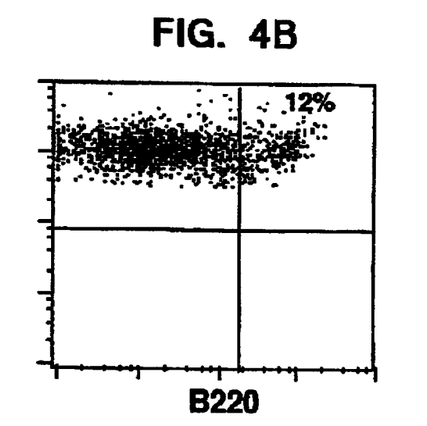
Figure 4C:
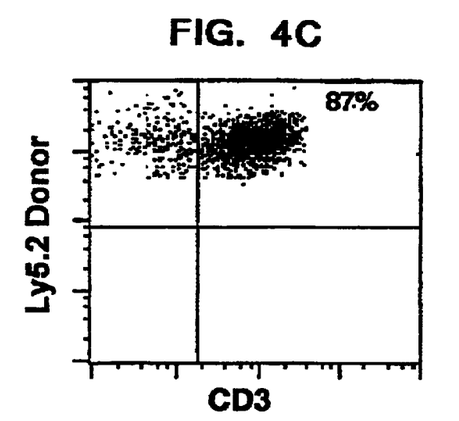
Figure 4D:
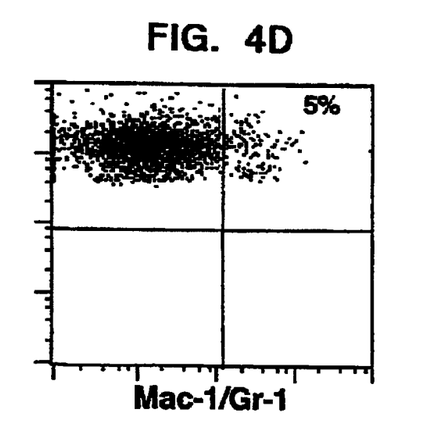

As early as 21 days after the transplant of a VC graft, up to 67% of the cells in the circulation of recipient mice were donor derived (FIG. 4A). When the spleens of vascular graft recipients were evaluated 4 months after transplant, multi-lineage donor derived hematopoiesis was routinely observed (FIGS. 4B–D). These results demonstrate that vascular derived donor cells contribute significantly to early hematopoietic reconstitution and persist long term, for at least 4 months, in the recipient animals.

Figure 5:
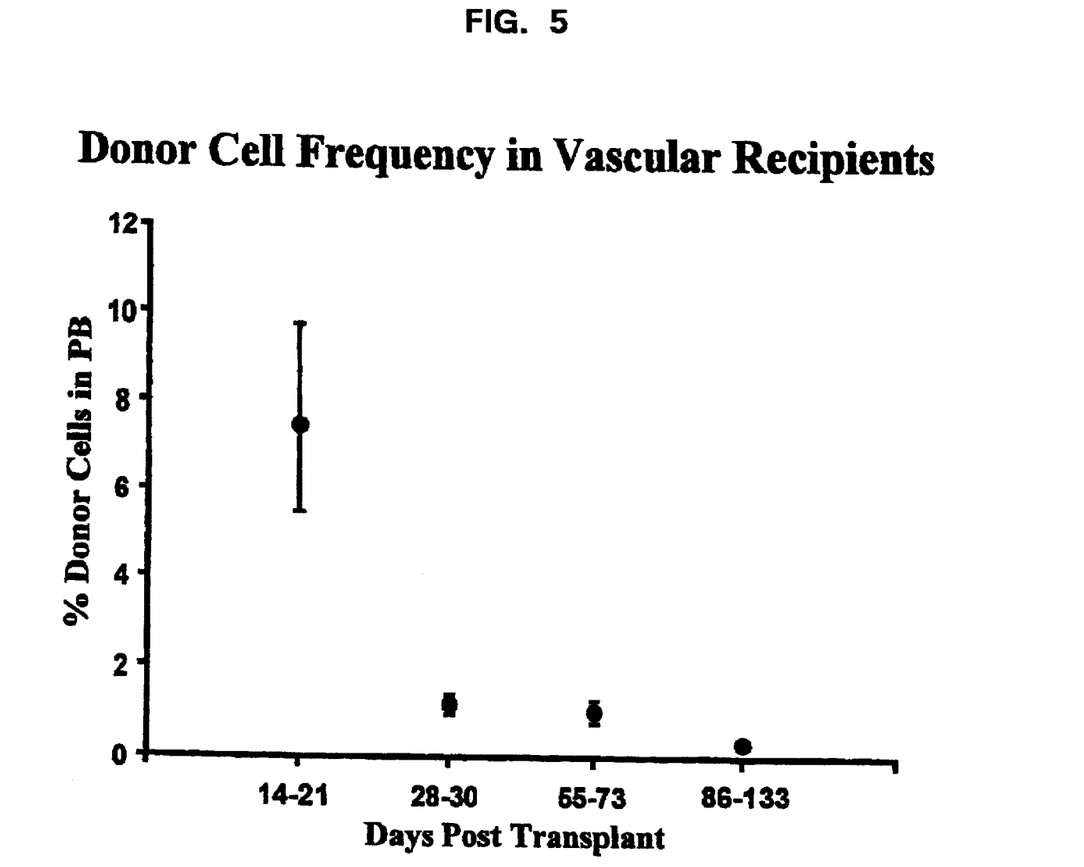
FIG. 5 is a graph showing the percentage of donor derived cells in the peripheral blood. Irradiated cogenic recipients were transplanted with 4 mm thoracic aorta (TA), vena cava (VC) or abdominal aorta (AA) grafts under the kidney capsule and the presence of donor cells was analyzed at the time points indicated. The percentage of Ly5.2 (donor) cells is shown. Data is shown as the mean±SEM. Five to 11 vascular recipients were analyzed per group.

However, although the vascular derived donor cells can contribute significantly to early hematopoietic reconstitution, recipient cells could also play a role in hematopoiesis. Thus, additional transplantations were performed using donor and recipient mice that were congenic at the Ly5 focus (CD45). Ly5.2 donor VC or TA grafts were implanted under the kidney capsule of irradiated Ly5.1 recipients. The percentage of Ly5.2 donor cells present in the peripheral blood was then evaluated (see FIG. 5). The results demonstrated that recipient cells could also participate in hematopoiesis. The results also demonstrate that the levels of donor cells decline over time. This indicates a very high degree of host recovery, and demonstrate a highly protective effect of components of the vascular graft on the host stem cells. This protective effect may be cytokine mediated. It should be noted that the use of higher doses of radiation can further compromise the host stem cells, and thus can ensure that donor cells predominate over time.

Example 7
Blood Vessel Derived Hematopoiesis in Other Tissues

The experiments described above were performed using the largest blood vessels found in the murine circulatory system. To determine whether cells with hematopoietic potential were found in differentiated tissues within the adult mouse, explants of normal ROSA26 adult heart and lung were transplanted into irradiated mice. Any means of sampling the vascularized tissue can be utilized to sample differentiated tissues, including surgical removal or punch biopsy. In the instant example, the tissue was dissected from donor animals, and a portion of the heart or lung (approximately 10 mg) was utilized. Fourteen days after transplantation, the recipients were sacrificed, and cross sections were prepared of the cardiac tissue or pulmonary tissue transplants.

Transplantation of cardiac or lung tissue into either the peritoneal space or under the kidney capsule stimulated the development of hematopoiesis. Thus, several transplantation sites can be used for the introduction of vascular tissue.

In histological sections prepared from the transplanted explants, thin walled vascular structures that appear to have coalesced together to form large vascular channels were routinely observed in explants of cardiac tissue. As with the thoracic aorta transplants (see Example 2), a significant population of migrating donor cells was observed following transplantation of ROSA26 lung tissue under the kidney capsule. Histologic evaluation of the transplanted lung tissue demonstrates the ROSA26 staining of donor cells is clearly distinguishable from host cells. Remarkably, as little as 10 mg of donor lung tissue or the equivalent of 50% of the total cardiac tissue from a single donor mouse conferred protection from lethal irradiation. The results demonstrate that hematopoietic cells arise from a number of highly vascular organs when these tissues are transplanted into an irradiated microenvironment that stimulates and supports hematopoietic stem cell differentiation.

Example 8

Localization of Early Proliferating Cells Within the Donor Vascular Tissue Explants To identify and purify the progenitor cell population of vascular tissue, the cellular proliferation within the vascular graft after transplantation was examined. Segments of proximal, inferior vena cava, (VC) or thoracic aorta (TA) were transplanted under the kidney capsule of irradiated (1100 cGy) or non-irradiated mice. Recipients were treated wit bromodeoxyuridine (BrdU) and the kidney containing the vascular graft was removed, fixed and evaluated for the uptake of BrdU by immunochemistry. As early as 48 hours after transplantation, BrdU positive, proliferating cells were identified in the endothelial layer of both the TA and VA grafts transplanted into irradiated recipients. In contrast, BrdU labeled cells were not identified following transplantation into non-irradiated mice. To ensure that nonspecific binding of the BrdU antibody was not induced by transplantation into irradiated animals, tissue sections were incubated with DAB substrate or VIP substrate. No positive cells were observed in the absence of the primary antibody to BrdU.

These results demonstrate that the transplantation of donor vascular tissue into irradiated animals leads to the proliferation of a population of cells within the intima of the transplanted vessel wall by 48 hours. In addition, the absence of BrdU positive cells in the intima of vascular grafts in non-irradiated mice indicates that the proliferation of this cell population(s) is dependent on specific signals in the immunocompromised recipient.

Thus, BrdU can be used to readily detect an anatomically distinct population of proliferating cells in transplanted vascular grafts. In addition the bone marrow, spleen, liver and thymus are examined for proliferating donor derived cells beginning as early as 24 hours after transplantation of the vascular tissue. To confirm that the BrdU identified cells are the progenitor cells, the cells are purified (using HO33342). HO33342 is a viable dye that stains DNA (Fleming et al., J. Cell. Biol. 122:897, 1993). This dye is used in conjunction with FACS to sort cells that are actively cycling (as compared to cell in G0/G1 phase of the cell cycle). The sorted cells can then be transplanted into recipient animals and their developmental potential.

Taken together, these studies described above demonstrate that hematopoietic progenitor/stem cells are present in the vascular tissue of normal adult animals.

Example 9

Evaluation of the Expression of Hematopoietic Cell and Vascular Markers on Donor Cells in the Transplanted Vascular Tissue Over the last few years, several cell surface markers have been found to be useful for the enrichment of HSC. Using combinations of these markers in conjunction with intracellular markers indicative of a quiescent non-proliferating cells (rhodamine low, Hoeschst low) it has been shown that the injection of as few as 5 cells can continuously give rise to more than 50% of the mature cells in the peripheral blood (e.g. see Morrison and Weissman, Immunity 1:661–673, 1994). In order to identify a candidate stem cell population from the vascular grafts, the phenotype of the cells that arise within the wall of the transplanted blood vessels is analyzed. The cell cycle status of donor cells is used as a guide to determine to localize cell populations that have the earliest proliferative response to the microenvironment of an irradiated host. Using immunohistochemical techniques, cells are localized within the transplanted vascular tissue that express several well described HSC markers including Sca-1, c-kit and AA.41. Cell surface markers of endothelial progenitors including Flk-1, TIE, TEK and TAL will similarly be assayed in the grafted vascular tissue. In the event that a particular marker is not detected in at least some cells by immunochemistry, in situ hybridization studies are performed to confirm this finding. In addition, ROSA26 donor mice are employed to demonstrate that these phenotypically defined cell populations are derived from the vascular graft donor and not a population of host cells that have subsequently migrated into the transplanted vascular tissue.

Immunochemistry provides tissue specific localization of phenotypically defined cells within the transplanted vascular graft. The primary limitation of this technique is that it is difficult to study the co-expression of more than 2 markers on an individual cell. To overcome this limitation, flow cytometry is used to examine the simultaneous expression of up to 4 cell surface markers on individual donor cells. Suspensions of cells are prepared from the vascular grafts and incubated with the antibodies listed above and analyzed by flow cytometry, in order to accurately quantitate the frequency of combinations of hematopoietic and vascular cell surface marker expression (see below, Example 11). To confirm that phenotypically defined cells are donor derived, the cell population of interest is sorted using a FACS Vantage cell sorter. The purity of the sorted product is evaluated by re-analysis of the sorted cells. Cytospin preparations are made and phenotypically defined cells are incubated with X-gal to demonstrate the presence of the ROSA26 donor cell marker. These combined approaches identify cell populations that express HSC markers, vascular progenitor markers or a combination of both in vascular tissue grafts. Normal, non-transplanted VC and TA are also assessed for the presence of these phenotypically defined progenitors.

Example 10

Functional Analysis of Blood Vessel Derived, Candidate Hematopoietic Progenitor/stem Cells The phenotypic analysis outlined above (Example 9) identifies cell populations that express cell surface markers associated with both vascular progenitors and hematopoietic cell progenitors. The expression of these cell markers is then utilized to identify and isolate candidate hematopoietic progenitor cells that arise in the transplanted vascular tissue. When determining whether a specfic combination of cell surface markers are informative for the identification of hematopoietic progenitor cells, it is important to ensure that a subpopulation of functional donor cells is not excluded by this approach. Therefore, donor derived cells are isolated from the wall of the vascular tissue implants and evaluated for the functional activity of each cell surface marker independently.

The minimum number of total donor derived vascular cells required to protect a recipient mouse from lethal irradiation is determined by limiting dilution analysis. Using cell sorting for a particular hematopoietic stem cell marker (e.g. Sca-1), populations of Sca-1+ cells and Sca-1− cells are purified. Proportionate numbers of each population are then injected into irradiated recipient mice. For instance, if it is determined that $1 \times 10^6$ total vascular cells are required to provide radioprotection, and the frequency of Sca-$1^+$ cells in the vascular cell population to be tested is 10%, then following cell sorting, one group of mice is transplanted with $1 \times 10^5$ Sca-$1^+$ cells and the second cohort of mice receives $9 \times 10^5$ Sca-$1^-$ cells. If Sca-1 marks the majority of cells with hematopoietic progenitor cell activity, then all mice transplanted with $1 \times 10^5$ Sca-$1^+$ cells would be expected to survive.

However, if Sca-1 expression is not found on these progenitor cells, then the radioprotective capacity would be confined to the Sca-$1^-$ cell populations. Survival of recipients of both $1 \times 10^5$ Sca-$1^+$ cells and $1 \times 10^5$ Sca-$1^-$ cells indicates that Sca-1 is not an informative marker of HSC activity in this system. Using this approach the utility of c-kit, AA.41, TIE1, TEK, Flk-1 and TAL will be tested for HSC activity. Combinations of these markers will be evaluated to further define this population.

This approach utilizes radioprotection as an assay for HSC activity. To ensure that multipotent cells that do not have the capacity for radioprotection but will read out in a multilineage hematopoietic assay are not excluded from analysis, irradiated recipient mice are injected with a limiting dose of marked (host) bone marrow to ensure radioprotection ($1 \times 10^5$ cells/mouse) and an appropriate number of vascular donor cells. The blood, bone marrow and spleen of these recipient mice are evaluated for the presence of donor cells at 1 and at 6 months post transplant. This competitive repopulation assay allows for the identification of blood vessel derived cells that have a functional capacity to repopulate irradiated hosts independent of the requirement of providing radioprotection.

Example 11
Further Characterization and Isolation of a Stem Cell from Transplanted Vascular Tissue and the Use of these Stem Cells Vascular tissue is transplanted into a subject as described above. In one embodiment, human vascular tissue (e.g. a portion of a saphenous vein, a portion of a mammary artery, or a piece of lung tissue obtained by biopsy) is transplanted into an immunocompromised mouse (e.g. a SCID mouse).

Various techniques are then employed to separate the cells by initially removing cells of dedicated lineage (see U.S. Pat. No. 5,914,108). Monoclonal antibodies are particularly useful for identifying markers (surface membrane proteins) associated with particular cell lineages (termed "lin" antibodies, and a cell which does not express these marker is term a "lin" cell) and/or stages of differentiation. The antibodies may be attached to a solid support to allow for crude separation. The separation techniques employed should maximize the retention of viability of the fraction to be collected. For "relatively crude" separations, that is, separations where up to 10%, usually not more than about 5%, preferably not more than about 1%, of the total cells present having the marker, may remain with the cell population to be retained, various techniques of different efficacy may be employed. The particular technique employed will depend upon efficiency of separation, cytotoxicity of the methodology, ease and speed of performance, and necessity for sophisticated equipment and/or technical skill.

Procedures for separation may include magnetic separation, using antibody-coated magnetic beads, affinity chromatography, cytotoxic agents joined to a monoclonal antibody or used in conjunction with a monoclonal antibody, e.g., complement and cytotoxins, and "panning" with antibody attached to a solid matrix, e.g., plate, or other convenient technique. Techniques providing accurate separation include fluorescence activated cell sorters, which can have varying degrees of sophistication, e.g., a plurality of color channels, low angle and obtuse light scattering detecting channels, impedance channels, etc.

One procedure utilized with human vascular tissue transplanted into a immunocompromised host is incubating the cells recovered from spleen or bone marrow at reduced temperatures, generally about 4° C., with saturating levels of antibodies specific for a particular cell type (e.g., CD3 and 8 for T-cell determinants). The cells are then washed with a fetal calf serum (FCS) cushion. The cells are suspended in a buffer medium and separated by means of the antibodies for the particular determinants, using various proteins specific for the antibodies or antibody-antigen complex.

Conveniently, the antibodies may be conjugated with markers, such as magnetic beads, which allow for direct separation, biotin, which can be removed with avidin or streptavidin bound to a support, fluorochromes, which can be used with a fluorescence activated cell sorter, or the like, to allow for ease of separation of the particular cell type. Any technique may be employed which is not unduly detrimental to the viability of the remaining cells.

After substantial enrichment of the cells lacking the mature cell markers, generally by at least about 50%, or at least about 70%, the cells may now be separated by a fluorescence activated cell sorter (FACS) or other methodology having high specificity. Multi-color analyses may be employed with the FACS. The cells are separated on the basis of the level of staining for the particular antigens.

In one embodiment, in a first separation, starting with at least about $1 \times 10^{10}$ to $3 \times 10^{10}$ cells, antibodies are used for the various dedicated lineages (B cell T cell, macrophage, etc.). These antibodies are each conjugated to different fluorochromes. Fluorochromes which may find use in a multi-color analysis include phycobiliproteins, e.g., phycoerythrin and allophycocyanins, fluorescein, Texas red, etc. While each of the lineages may be separated in a separate step, it is also possible to separate the lineages are separated at the same time. Generally, the number of cells obtained will be fewer than about 1% of the original cells, generally fewer than about 0.5% and may be as low as 0.2% or less.

The cells can also be further separated by positively selecting for the expression of Thy (Thy$^+$), where the cells will generally be fewer than 0.5% of the original cells, generally in the range of 0.01–0.5%. The cells may be selected against dead cells, by employing dyes associated with dead cells (propidium iodide, LDS). In one embodiment, the cells are collected in a medium comprising 2% fetal calf serum. Other techniques for positive selection may be employed, which permit accurate separation, such as affinity columns, and the like. The method should permit the removal to a residual amount of less than about 20%, preferably less than about 5%, of the non-stem cell populations.

In one embodiment, the cells are also selected for the expression of a known stem cell antigen. In a specific, non-limiting example, cells derived from human vascular tissue are selected for the expression of CD34.

In another embodiment cells are selected based on light-scatter properties as well as their expression of various cell surface antigens. In one specific non-limiting example CD34$^+$Lin$^-$ and the CD34$^+$Lin$^-$Thy-$1^+$ have low side scatter and low forward scatter profiles by FACS analysis. Cytospin preparations show the stem cell to have a size between mature lymphoid cells and mature granulocytes. Cells of interest are thus isolated base on the side and forward scatter profile.

In general, the particular order of separation is not critical. However, in one embodiment, the cells are initially separated by a coarse separation, followed by a fine separation, negative selection for markers associated with lineage committed cells. If positive selection of a marker associated with stem cells is utilized, it is performed at the same time as the negative selection, or following negative selection. This separation is followed by an assay to determine if the cellular composition has multi-lineage potential and enhanced self-regeneration capability.

An isolated cell is then tested to determine if it provides for production of myeloid cells and lymphoid cells in appropriate cultures. In one embodiment cultures providing hydrocortisone for production of myeloid cells (Dexter-type cultures) are used. In another embodiment, cultures for B lymphocytes, lacking hydrocortisone (Whitlock-Witte type cultures), are used. In each of the cultures, stromal cells are provided (e.g. mouse or human stromal cells). In one embodiment, the stromal cells are mouse or human and come from various strains (e.g. AC3 or AC6), or the stromal cells are derived from mouse or human fetal bone marrow by selection for the ability to maintain human stem cells, and the like. The medium employed for the culturing of the cells is conveniently a defined enriched medium, such as IMDM (Iscove's Modified Dulbecco's Medium), a 50:50 mixture of IMDM and RPMI, and will generally be composed of salts, amino acids, vitamins, $5 \times 10^{-5}$ M 2-ME (beta mercaptoethanol), streptomycin/penicillin, and 10% fetal calf serum. The media is changed from time to time, generally at least about once to twice per week. In one procedure, by transferring cells from one culture with hydrocortisone, to the other culture without hydrocortisone, and demonstrating the production of members of the different lineages in the different cultures, the presence of the stem cell and its maintenance is supported. In this manner, the production of both myeloid cells and B-cells is demonstrated.

In identifying myeloid and B-cell capability, the population to be tested is introduced first into a hydrocortisone containing culture and allowed to grow for six weeks in such culture. In one embodiment, the medium employed includes a 50:50 mixture of RPMI 1640 and IMDM containing 10% FCS, 10% horse serum, streptomycin/penicillin, glutamine, and 5×10:1M hydrocortisone. During a six week period, in the absence of progenitor cells all of the mature cells would die. However, if at the end of six weeks, myeloid cells are still observed, a progenitor cell is present which provides for the continuous differentiation to myeloid cells. At this time, the medium is changed, so that the medium now lacks hydrocortisone, an the growth of B-cells is thus selected. After 3–4 weeks the presence of B-cells is demonstrated by FACS analysis. If the presence of B cells is demonstrated, then the progenitor cells which are capable of producing myeloid cells are also capable of producing B-cells.

To demonstrate differentiation to T-cells, fetal thymus is isolated (e.g. mouse fetal thymus, human fetal thymus from abortion tissue, pig, monkey, sheep, cow, rat, or rabbit fetal thymus) and the thymus is cultured for 4–7 days at about 25° C. in order to deplete the lymphoid population of the fetal thymus. The cells to be tested are then microinjected into the thymus tissue, where the HLA of the population which is injected is mismatched with the HLA of the thymus cells.

The thymus tissue may then be transplanted into a scid/scid mouse as described in EPA 0 322 240, particularly transplanting in the kidney capsule.

In order to determine if a cell can differentiate into red blood cells, conventional techniques can be used to identify BFU-E units, for example methylcellulose culture (Metcalf (1977) In: Recent Results in Cancer Research 61. Springer-Verlag, Berlin, pp 1–227). The procedures demonstrate that the cells are capable of developing the erythroid lineage.

Once stem cells have been isolated, they are propagated by growing in conditioned medium from stromal cells, such as stromal cells that can be obtained from bone marrow, fetal thymus or fetal liver, and are shown to provide for the secretion of growth factors associated with stem cell maintenance, coculturing with such stromal cells, or in medium comprising maintenance factors supporting the proliferation of stem cells. The stromal cells may be allogeneic or xenogeneic. Before using in the coculture, the mixed stromal cell preparations may be freed of hematopoietic cells employing appropriate monoclonal antibodies for removal of the undesired cells, e.g, with antibody-toxin conjugates, antibody and complement, etc. Alternatively, cloned stromal cell lines may be used where the stromal lines may be allogeneic or xenogeneic.

Stem cells obtained using these methods can be used in a variety of therapeutic treatments. In one embodiment, the cells are used to reconstitute fully an irradiated host and/or a host subject to chemotherapy. Stem cells can also be used as a source of cells for specific lineages, by providing for their maturation, proliferation and differentiation into one or more selected lineages by employing a variety of factors, such as erythropoietin, colony stimulating factors, e.g., GM-CSF, G-CSF, or M-CSF, interleukins, e.g., IL-1, -2, -3, -4, -5, -6, -7, -8, etc., Leukemia Inhibitory Factory (LIF), Steel Factor (SLF), or the like. Alternatively stromal cells associated with the stem cells becoming committed to a particular lineage, or with their proliferation, maturation and differentiation can be employed. The stem cells may also be used in the isolation and evaluation of factors associated with the differentiation and maturation of hematopoietic cells. Thus, the stem cells may be used in assays to determine the activity of media, such as conditioned media, evaluate fluids for cell growth activity, involvement with dedication of particular lineages, or the like.

The stem cells can be used for the treatment of genetic diseases. Genetic diseases associated with hematopoietic cells may be treated by genetic modification of autologous or allogeneic stem cells to correct the genetic defect. For example, diseases such as B-thalassemia, sickle cell anemia, adenosine deaminase deficiency, recombinase deficiency, recombinase regulatory gene deficiency, etc. may be corrected by introduction of a wild-type gene into the stem cells, either by homologous or random recombination. With allogeneic stem cells, normal cells lacking the genetic defect can be used as a therapy. Other indications of gene therapy are introduction of drug resistance genes to enable normal stem cells to have an advantage and be subject to selective pressure, e.g. the multiple drug resistance gene (MDR). Diseases other than those associated with hematopoietic cells may also be treated, where the disease is related to the lack of a particular secreted product such as a hormone, enzyme, interferon, factor, or the like. By employing an appropriate regulatory initiation region, inducible production of the deficient protein may be achieved, so that production of the protein will parallel natural production, even though production will be in a different cell type from the cell type that normally produces such protein. It is also possible to insert a ribozyme, antisense or other message to inhibit particular gene products or susceptibility to diseases, particularly hematolymphotropic diseases.

Alternatively, in order to remove a particular variable region of a T-cell receptor from the T-cell repertoire, homologous recombination, or antisense or ribozyme sequence which prevents expression is used to inhibit expression of the particular T-cell receptor may be inhibited. For treatment with hematotropic pathogens, such as HIV, HTLV-I and II, etc. the stem cells are genetically modified to introduce an antisense sequence or ribozyme which would prevent the proliferation of the pathogen in the stem cell or cells differentiated from the stem cells.

Methods for recombination in mammalian cells may be found in Molecular Cloning, A Laboratory Manual (1989) Sambrook, Fritsch and Maniatis, Cold Spring Harbor, N.Y.

Stem cells obtained using a model system or a method of the invention may be frozen at liquid nitrogen temperatures and stored for long periods of time, being thawed and capable of being reused. The cells will usually be stored in 10% DMSO, 70% autologous plasma (irradiated with 2500 rad), 20% Tcl99 (Tissue culture medium). Cells are frozen in a programmable cell for to −180.degree. C. in liquid nitrogen. Once thawed, the cells may be expanded by use of growth factors or stromal cells associated with stem cell proliferation and differentiation.

The hematopoietic stem cells, either autologous or allogeneic, may be used for treatment of various diseases where toxic therapies may be involved. For example, in the treatment of neoplasia, bone marrow may be removed from the patient (autologous) or from a "matched" donor ("allogeneic") and the stem cells isolated and optimally frozen. The patient's bone marrow may be partially or wholly ablated using irradiation and/or chemotherapy. Once the treatment is completed, the stem cells may be thawed, if appropriate, administered to the patient by any convenient means, e.g., intravascularly, in a physiologically acceptable medium. The patient may then be monitored for signs of engraftment.

The stem cells may be grown in culture, whereby the stem cells may be expanded. In this way, one can repetitively administer stem cells during a course of a toxic therapy. In addition, the expanded stem cells can be used to study growth factors in culture, or can be used to test a method of introducing exogenous nucleic acid into stem cells.

Example 12

Using Transplants of Vascular Tissue to Isolate Growth Factors

The transplantation of vascular tissue into immunocompromised subjects may also be used to isolation and evaluate factors associated with the growth, differentiation and maturation of hematopoietic cells. Thus, the grafts are harvested from the recipients, and are then placed in culture and used in assays to determine the activity of media, such as conditioned media, evaluate fluids for growth factor activity, involvement with dedication of lineages, or the like. The subject grafts may also be used in the identification of supportive cells for the isolation and evaluation of factors associated with the self-renewal of hematopoietic cells. Thus, the model system of the invention may be used in assays to determine either autocrine or paracrine regulatory signals and evaluate responses to growth factor either from external or intrinsic protein sources; and to determine the activity of media, such as conditioned media, evaluate fluids for cell growth activity, involvement with dedication of particular lineages, or the like.

The grafted vascular tissue produces and/or is responsive to a factor that permits migration and replication of hematopoietic stem cells. This factor may be isolated from biological samples isolated from recipient subjects, by separating or fractionating (e.g. chromatographically) a biological fluid (e.g. blood), or by sampling, and extracting a biopsy sample. Alternatively, a tissue sample (e.g. a graft 14 days after transplantation) is harvested from a recipient and cultured in vitro, and conditioned media is collected. In one embodiment, the conditioned media or biological sample is fractionated. The active fraction containing the desired factor is identified by measuring the growth and differentiation of stem cells in the presence and absence of such fractions, or alternatively, using comparative analysis of fluid.

Thus, in a yet further embodiment, the invention provides for a stem cell growth factor, characterized as facilitating and/or promoting growth of a stem cell population and/or protecting the stem cell from the effects of lethal irradiation. This factor is further characterized in that it is capable of being isolated from a vascular graft or an extract thereof, such as a supernatant form an in vitro culture derived from a vascular graft. The factor thus isolated is preferably in pure or substantially pure form, e.g. at least 90%, preferably at least 95%, most preferably at least 99% pure form.

A factor that protects normal stem cells from lethal irradiation may have a variety of clinical applications (e.g. to rescue the marrow of humans exposed to lethal irradiation, or to treat patients with hematologic malignancies, such as by protecting normal stem cells while abnormal cells are removed).

Having illustrated and described the principles of using vascular tissue to enhance hematopoeisis in a subject, the art of the invention can be modified in arrangement and detail without departing from such principles. In view of the many possible embodiments to which the principles of my invention can be applied, it should be recognized that the illustrated embodiments are only examples of the invention and should not be taken as a limitation on the scope of the invention. Rather, the scope of the invention is in accord with the following claims. I therefore claim as my invention all that comes within the scope and spirit of these claims.

I claim:

1. A method for enhancing hematopoiesis in a subject deficient in hematopoiesis, comprising:

transplanting a therapeutically effective portion of an isolated adult vascular tissue into a subject deficient in hematopoeisis, wherein the isolated adult vascular tissue enhances hematopoiesis in the subject.

2. The method of claim 1, wherein the isolated adult vascular tissue is autologous vascular tissue.

3. The method of claim 1, wherein the isolated adult vascular tissue is heterologous vascular tissue.

4. The method of claim 1, wherein the subject is deficient in hematopoiesis due to irradiation.

5. The method of claim 1, Wherein the subject is deficient in hematopoiesis due to a genetic immunodeficiency, irradiation, chemotherapy, or neutropenia.

6. The method of claim 1, wherein the portion of the isolated vascular tissue is a portion of an artery or a vein.

7. The method of claim 1, wherein the isolated vascular tissue is a portion of a vena cava, a thoracic aorta, an artery, a vein, or a capillary of a microvascular circulation.

8. The method of claim 1, wherein hematopoiesis is enhanced by a cell or factor provided by the transplanted vascular tissue.

9. The method of claim 1, wherein the subject is a mammalian subject.

10. The method of claim 9, wherein the subject is a mouse, a human, a monkey, a cow, a pig, a sheep, a rat, or a rabbit.

11. The method of claim 1, wherein the vascular tissue is transplanted under the kidney capsule.

12. The method of claim 1, wherein the vascular tissue is transplanted intraperitoneally or subcutaneously.

13. The method of claim 1, wherein the vascular tissue does not form an enclosed lumen.

14. The method of claim 1, further comprising assaying hematopoiesis in a sample from the subject.

15. The method of claim 1, wherein the isolated adult vascular tissue comprises a portion of an artery or vein.

16. The method of claim 1, wherein the subject is a non-human animal subject.

* * * * *

UNITED STATES PATENT AND TRADEMARK OFFICE
CERTIFICATE OF CORRECTION

PATENT NO. : 6,821,513 B1
DATED : November 23, 2004
INVENTOR(S) : William H. Fleming It is certified that error appears in the above-identified patent and that said Letters Patent is hereby corrected as shown below:

Column 1,
Lines 6-7, "PCT/US00/17427 Jun. 22, 2000" should read -- PCT/US00/17427 filed Jun. 22, 2000 --.

Column 6,
Line 38, "strong" should read -- stromal --.

Column 9,
Line 24, "animal" should read -- mammal --.

Column 10,
Line 19, "vial tubes," should read -- vials, tubes, --.
Line 45, "distal aorta" should read -- dorsal aorta --.
Line 61, "Modem" should read -- Modern --.

Column 14,
Line 5, "Reconstruction" should read -- Reconstitution --.
Line 32, "focus" should read -- locus --.

Column 21,
Line 22, "cell for to - 180.degree.C." should read -- cell freezer to - 180.degree.C. --.

Signed and Sealed this

Fourteenth Day of June, 2005

JON W. DUDAS
*Director of the United States Patent and Trademark Office*